(12) United States Patent
Imai

(10) Patent No.: US 11,771,404 B2
(45) Date of Patent: *Oct. 3, 2023

(54) ACOUSTIC WAVE DIAGNOSTIC APPARATUS AND CONTROL METHOD THEREOF

(71) Applicant: FUJIFILM Corporation, Tokyo (JP)

(72) Inventor: Yoshiro Imai, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 18/046,786

(22) Filed: Oct. 14, 2022

(65) Prior Publication Data

US 2023/0064315 A1 Mar. 2, 2023

Related U.S. Application Data

(63) Continuation of application No. 15/941,178, filed on Mar. 30, 2018, now Pat. No. 11,497,477, which is a
(Continued)

(30) Foreign Application Priority Data

Oct. 1, 2015 (JP) .................................. 2015-196268

(51) Int. Cl.
*A61B 8/00* (2006.01)
*A61B 8/08* (2006.01)
*A61B 8/14* (2006.01)

(52) U.S. Cl.
CPC .................. *A61B 8/54* (2013.01); *A61B 8/08* (2013.01); *A61B 8/085* (2013.01); *A61B 8/0883* (2013.01);
(Continued)

(58) Field of Classification Search
CPC ........... A61B 8/54; A61B 8/0883; A61B 8/14; A61B 8/485; A61B 8/5276; A61B 8/5284
See application file for complete search history.

(56) References Cited

U.S. PATENT DOCUMENTS 5,873,830 A 2/1999 Hossack et al.
6,312,382 B1 * 11/2001 Mucci ................. G01S 7/52036
600/437
(Continued)

FOREIGN PATENT DOCUMENTS

EP 1891900 A1 2/2008
JP 3268396 B2 3/2002
(Continued)

OTHER PUBLICATIONS

Advisory Action issued in U.S. Appl. No. 15/941,178 dated Apr. 5, 2022.
(Continued)

*Primary Examiner* — Patricia J Park
*Assistant Examiner* — Adil Partap S Virk
(74) *Attorney, Agent, or Firm* — Birch, Stewart, Kolasch & Birch, LLP

(57) ABSTRACT

Periodic displacement occurs in body tissue due to heartbeat. A peak level D of the movement distance of the body tissue is detected (Step 21), and a heartbeat cycle T is calculated from a frequency spectrum (Steps 22 and 23). By dividing twice the peak level D by the heartbeat cycle T, the moving velocity of the body tissue in a unit heartbeat cycle is calculated (Step 24). By dividing the moving velocity by a frame rate r, an average movement distance of the body tissue between frames is calculated (Step 25). In a case where the average movement distance is smaller than a predetermined threshold value, a time interval between the
(Continued)

frames used for the calculation of the movement distance is extended (being Step 26 NO, Step 27).

2 Claims, 9 Drawing Sheets

Related U.S. Application Data continuation of application No. PCT/JP2016/077765, filed on Sep. 21, 2016.

(52) U.S. Cl.
CPC ............... *A61B 8/14* (2013.01); *A61B 8/485* (2013.01); *A61B 8/5276* (2013.01); *A61B 8/5284* (2013.01); *A61B 8/543* (2013.01)

(56) References Cited

U.S. PATENT DOCUMENTS

| | | | |
|---|---|---|---|
| 11,497,477 B2* | 11/2022 | Imai | A61B 8/0883 |
| 2001/0024516 A1* | 9/2001 | Yoshioka | G01S 7/52073 382/128 |
| 2006/0241510 A1 | 10/2006 | Halperin et al. | |
| 2007/0167777 A1 | 7/2007 | Abe et al. | |
| 2007/0248319 A1 | 10/2007 | Sakaguchi | |
| 2007/0297694 A1 | 12/2007 | Kurata | |
| 2008/0139935 A1 | 6/2008 | Lin et al. | |
| 2008/0188743 A1 | 8/2008 | Waki et al. | |
| 2009/0292205 A1 | 11/2009 | Osaka | |
| 2010/0208957 A1 | 8/2010 | Chen et al. | |
| 2011/0098563 A1* | 4/2011 | Osaka | A61B 8/08 600/438 |
| 2012/0253195 A1* | 10/2012 | Inoue | G01S 7/52036 600/438 |
| 2014/0051998 A1 | 2/2014 | Shimazaki | |
| 2014/0276104 A1 | 9/2014 | Tao et al. | |
| 2015/0272547 A1 | 10/2015 | Freiburger et al. | |
| 2015/0342571 A1 | 12/2015 | Ohuchi et al. | |

FOREIGN PATENT DOCUMENTS

| | | |
|---|---|---|
| JP | 2003-250767 A | 9/2003 |
| JP | 2003-284718 A | 10/2003 |
| JP | 2006-181058 A | 7/2006 |
| JP | 2008-142540 A | 6/2008 |
| JP | 2008-167838 A | 7/2008 |
| JP | 2010-22418 A | 2/2010 |
| JP | 2012-75950 A | 4/2012 |
| JP | 2013-240721 A | 12/2013 |
| JP | 2014-36778 A | 2/2014 |
| JP | 2014-144370 A | 8/2014 |
| WO | WO 2011/096556 A1 | 8/2011 |

OTHER PUBLICATIONS

Advisory Action issued in U.S. Appl. No. 15/941,178 dated Aug. 30, 2021.
Advisory Action issued in U.S. Appl. No. 15/941,178 dated Dec. 4, 2020.
English translation of Tsujita Document (WO 2011096556) (Year: 2011); 24 pages.
Extended European Search Report for European Application No. 16851287.9, dated Sep. 26, 2018.
Final Office Action issued in U.S. Appl. No. 15/941,178 dated Jan. 18, 2022.
Final Office Action issued in U.S. Appl. No. 15/941,178 dated Jun. 8, 2021.
Final Office Action issued in U.S. Appl. No. 15/941,178 dated Sep. 28, 2020.
International Preliminary Report on Patentability and Written Opinion of the International Searching Authority (forms PCT/IB/373, PCT/ISA/237 and PCT/IB/326), dated Apr. 12, 2018, for International Application No. PCT/JP2016/077765, with an English translation of the Written Opinion.
International Search Report (form PCT/ISA/210), dated Nov. 22, 2016, for International Application No. PCT/JP2016/077765, with an English translation.
Non-Final Office Action issued in U.S. Appl. No. 15/941,178 dated Apr. 6, 2020.
Non-Final Office Action issued in U.S. Appl. No. 15/941,178 dated Feb. 18, 2021.
Non-Final Office Action issued in U.S. Appl. No. 15/941,178 dated Sep. 22, 2021.
Notice of Allowance issued in U.S. Appl. No. 15/941,178 dated Jul. 12, 2022.
Thomas Nelson, et al, "Three-Dimensional Echocardiographic Evaluation of Fetal Heart Anatomy and Functions: Acquisition, Analysis, and Display", 1996, American Institute of Ultrasound in Medicine, Journal Ultrasound Medicine, 15:1-9, pp. 1-9 (Year: 1996).

\* cited by examiner

ELASTIC IMAGE (FAST HEARTBEAT)

ELASTIC IMAGE (SLOW HEARTBEAT)

FRAME RATE $\alpha$      FRAME RATE $\beta$

FRAME RATE $\alpha$ > FRAME RATE $\beta$

CALCULATE MOVEMENT DISTANCE FROM FRAME T−1 AND FRAME T, FRAME T AND FRAME T+1      CALCULATE MOVEMENT DISTANCE FROM FRAME T−1 AND FRAME T+1

ACOUSTIC WAVE DIAGNOSTIC APPARATUS AND CONTROL METHOD THEREOF

CROSS-REFERENCE TO RELATED APPLICATIONS

This application is a Continuation of U.S. application Ser. No. 15/941,178 filed Mar. 30, 2018, which is a Continuation of PCT International Application No. PCT/JP2016/077765 filed on Sep. 21, 2016, which claims priority under 35 U.S.C. § 119(a) to Japanese Patent Application No. 2015-196268 filed on Oct. 1, 2015. Each of the above applications is hereby expressly incorporated by reference, in its entirety, into the present application.

BACKGROUND OF THE INVENTION

1. Field of the Invention

The present invention relates to a diagnostic apparatus using, acoustic waves, for example, ultrasonic waves, and a control method thereof.

2. Description of the Related Art

Various diagnostic apparatuses using living body information for medical diagnosis have been developed (JP2014-36778A, JP3268396B, JP2010-22418A, JP2012-75950A, JP2008-167838A, JP2006-181058A, JP2003-284718A, and JP2003-250767A). In recent years, information (strain) on the hardness or softness of body tissue has been measured using ultrasonic waves, and elastography using this information for medical diagnosis has also been known. JP2014-36778A describes generating an elastic image representing the hardness (strain) of body tissue, using the movement of the body tissue resulting from heartbeat. As described in JP3268396B, in general, the movement of the body tissue is measured with the movement distance or displacement between respective points on two time-series tomograms. JP2010-22418A describes adjusting a frame rate with reference to a correspondence table according to the number of heartbeats per minute.

SUMMARY OF THE INVENTION

The rate or magnitude of the heartbeat varies depending on subjects (patients). For example, in the case of a subject with extremely slow heartbeat, the movement distance or displacement between the two time-series tomograms becomes small. As a result, accurate strain cannot be measured under the influence of flickering (noise) of signals. In this case, an elastic image representing the finally obtained strain also becomes inaccurate. Even in a case where the time interval between the two tomograms is excessively narrow (the frame rate is extremely high) with respect to the rate of the heartbeat, the movement distance or displacement between the two time-series tomograms becomes small. As a result, this case is also affected by the flickering (noise) of the signals.

An object of the invention is to maintain a high-accuracy elastic image with little noise or with no noise irrespective of the rate of the heartbeat of each of the subjects.

An acoustic wave diagnostic apparatus according to the invention comprises an acquisition device (acquisition means) for acquiring acoustic wave frame data at a predetermined frame rate, using an acoustic wave echo signal representing an acoustic wave echo reflected from body tissue of a subject; a movement distance calculating device (movement distance calculating means) for calculating a movement distance of the body tissue, using a pair of acoustic wave frame data items; an elastic image generating device (elastic image generating means) for generating an elastic image representing strain calculated from the movement distance of the body tissue calculated by the movement distance calculating device; a heartbeat cycle calculating device (heartbeat cycle calculating means) for calculating a heartbeat cycle of the subject; an average movement distance calculating device (average movement distance calculating means) for calculating an average movement distance of the body tissue between the acoustic wave frame data items in the heartbeat cycle of the subject, using the movement distance of the body tissue calculated from each of a plurality of pairs of acoustic wave frame data items by the movement distance calculating device and the heartbeat cycle of the subject calculated by the heartbeat cycle calculating device; and an adjusting device (adjusting means) for extending a time interval between the acoustic wave frame data items used for the calculation of the movement distance of the body tissue and the generation of the elastic image in a case where the average movement distance calculated by the average movement distance calculating device is smaller than a predetermined threshold value.

The invention also provides a control method suitable for the acoustic wave diagnostic apparatus. That is, this method comprises acquiring acoustic wave frame data at a predetermined frame rate by an acquisition device on the basis of an acoustic wave echo signal representing an acoustic wave echo reflected from body tissue of a subject; calculating a movement distance of the body tissue by a movement distance calculating device, using a pair of acoustic wave frame data items; generating, by an elastic image generating device, an elastic image representing strain calculated from the movement distance of the body tissue calculated by the movement distance calculating device; calculating a heartbeat cycle of the subject by a heartbeat cycle calculating device; calculating an average movement distance of the body tissue between the acoustic wave frame data items in the heartbeat cycle of the subject by an average movement distance calculating device, using the movement distance of the body tissue calculated from each of a plurality of pairs of acoustic wave frame data items by the movement distance calculating device and the heartbeat cycle of the subject calculated by the heartbeat cycle calculating device; and extending a time interval between the acoustic wave frame data items used for the calculation of the movement distance of the body tissue and the generation of the elastic image by an adjusting device in a case where the average movement distance calculated by the average movement distance calculating device is smaller than a predetermined threshold value.

As the time interval between the acoustic wave frame data items used for the calculation of the movement distance of the body tissue and the generation of the elastic image is extended, the average movement distance of the body tissue calculated by the average movement distance calculating device becomes large. In one embodiment, the time interval between the acoustic wave frame data items can be extended such that the average movement distance coincides with the threshold value (may not coincide perfectly and may coincide approximately).

Preferably, the acoustic wave diagnostic apparatus further comprises a region-of-interest setting device (region-of-interest setting means) for setting a portion of an acoustic wave image represented on the basis of the acoustic wave echo signal as a region of interest. The movement distance calculating device calculates the movement distance of the body tissue included in the region of interest set by the region-of-interest setting device.

In one aspect, the average movement distance calculating device obtains a heartbeat average velocity of the subject, using the movement distance of the body tissue calculated from each of the plurality of pairs of acoustic wave frame data items and the heartbeat cycle of the subject calculated by the heartbeat cycle calculating device, and calculates the average movement distance of the body tissue by dividing the heartbeat average velocity by the frame rate.

In another aspect, the plurality of pairs of acoustic wave frame data items are obtained over one heartbeat cycle of the subject, and the average movement distance calculating device calculates the average movement distance of the body tissue by taking an average of movement distances of the body tissue calculated from the plurality of pairs of acoustic wave frame data items, respectively.

Preferably, a movement distance immediately after the start of heartbeat and immediately before the end of the heartbeat among the movement distances of the body tissue calculated from the plurality of pairs of acoustic wave frame data items, respectively, over the one heartbeat cycle is excluded from the calculation of the average movement distance.

In one aspect, the adjusting device extends the time interval by lowering the frame rate of the acquisition device.

In another aspect, the adjusting device extends the time interval by thinning out and using the acoustic wave frame data used for the calculation of the movement distance of the body tissue from the acoustic wave frame data acquired by the acquisition device.

Advantage of the Invention

According to this invention, in a case where the average movement distance of the body tissue is smaller than the predetermined threshold value, the time interval between the acoustic wave frame data items used for the calculation of the movement distance of the body tissue and the generation of an elastic image is extended. Thus, the movement distance of the body tissue between the acoustic wave frame data items can be increased. As the movement distance of the body tissue between the acoustic wave frame data items is increased, it is possible to prevent or reduce the appearance of noise in the elastic image, and it is possible to maintain a high-accuracy elastic image.

DESCRIPTION OF THE PREFERRED EMBODIMENTS

Figure 1:
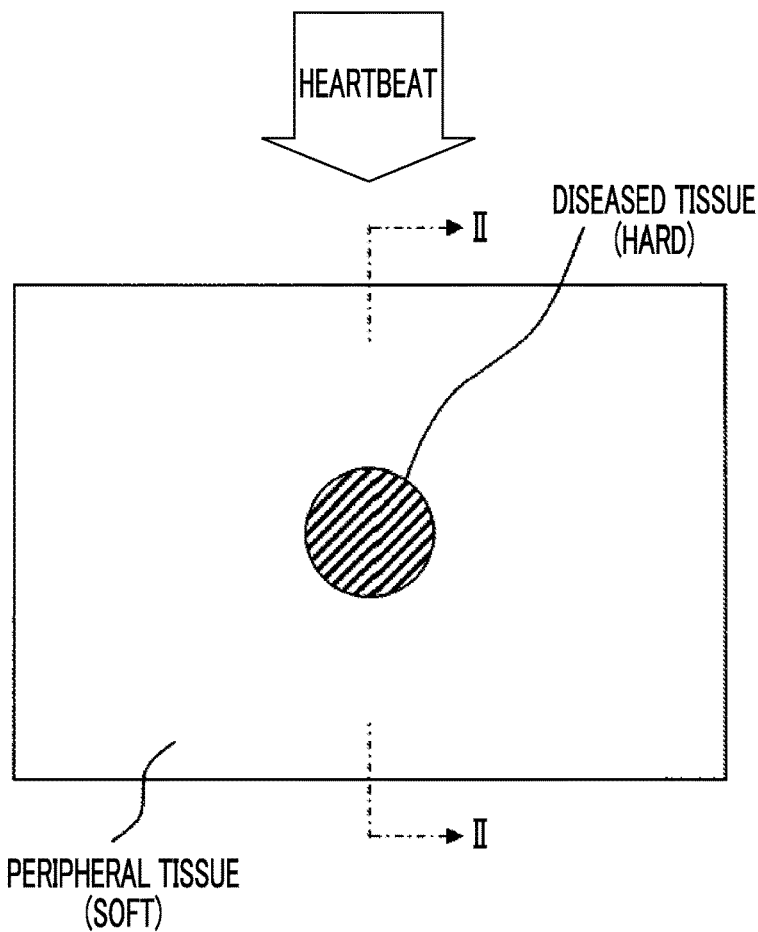
FIG. 1 schematically illustrates the inside of a living body where diseased tissue is present.
Figure 2:
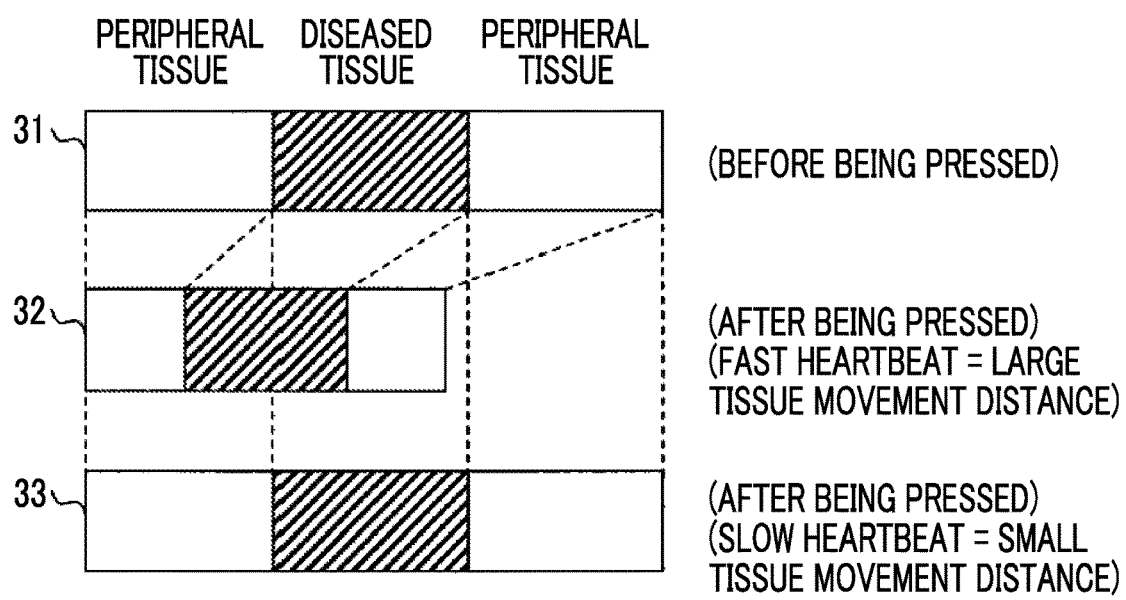
FIG. 2 illustrates the positions of peripheral tissue and the diseased tissue before being pressed, the positions of the peripheral tissue and the diseased tissue after being pressed in a case where movement distance is large, and the positions of the peripheral tissue and the diseased tissue after being pressed in a case where the movement distance is small.

First, elastic images will be schematically described with reference to FIG. 1 to FIG. 6. FIG. 1 schematically illustrates the inside of a living body where hard diseased tissue exists so as to be surrounded by soft peripheral tissue (normal body tissue). Reference sign 31 of FIG. 2 schematically represents the peripheral tissue and the diseased tissue before being pressed (at the time of relaxation) caused by heartbeat in a cross-sectional position along line II-II of FIG. 1, that is, passing through the diseased tissue. Reference signs 32 and 33 of FIG. 2 designate the peripheral tissue and the diseased tissue after being pressed (at the time of compression), reference sign 32 schematically designates a state where the peripheral tissue and the diseased tissue are greatly displaced due to heartbeat, and reference sign 33 schematically designates a state where the peripheral tissue and the diseased tissue are slightly displaced (a state in the middle of being displaced) due to heartbeat. In order to make this easily understood, FIG. 2 illustrates that a left end of the peripheral tissue is fixed (no displacement).

Figure 3:
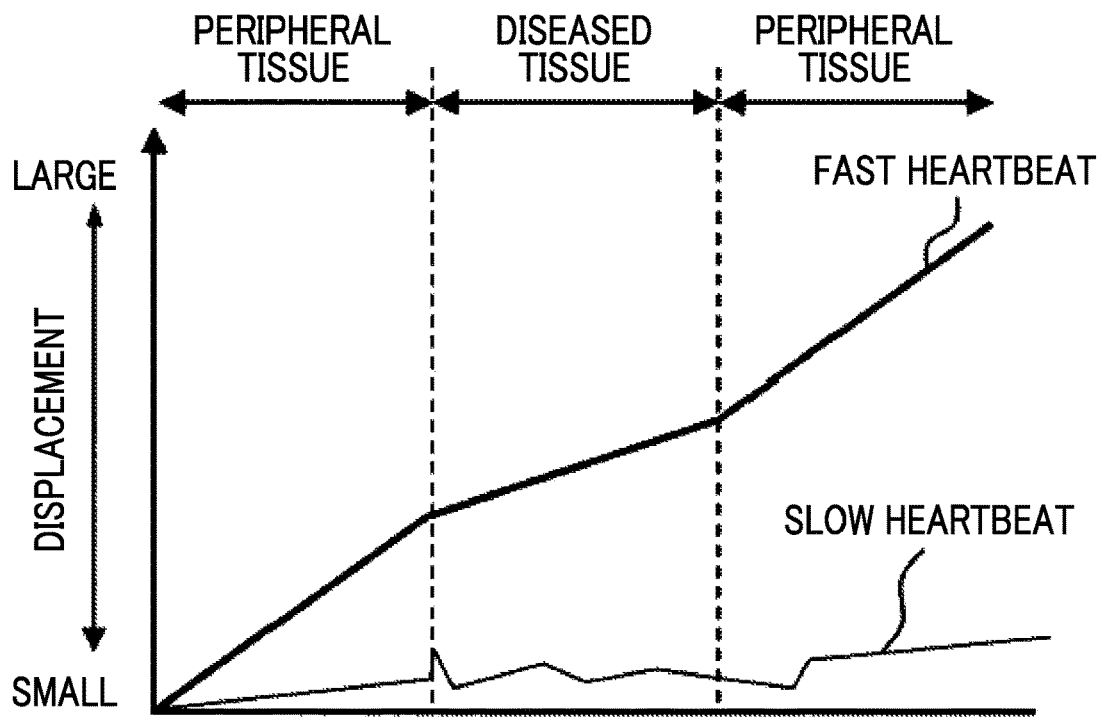
FIG. 3 is a graph illustrating the displacement of the peripheral tissue and the diseased tissue before and after being pressed.
Figure 4:
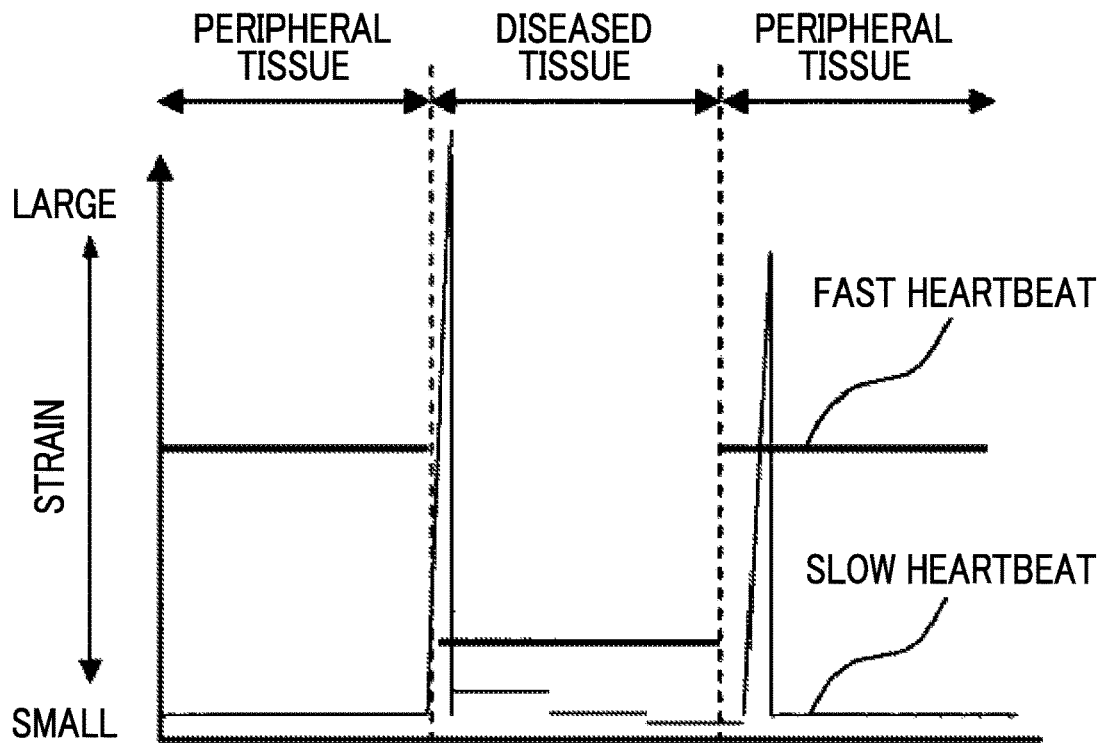
FIG. 4 is a graph illustrating the strain of the peripheral tissue and the diseased tissue before and after being pressed.

FIG. 3 is a graph graphically illustrating the displacement of the peripheral tissue and the diseased tissue before and after being pressed, which are respectively designated by reference signs 31 and 32 and reference signs 31 and 33 of FIG. 2. FIG. 4 is obtained by differentiating the displacement illustrated in FIG. 3. In FIGS. 3 and 4, graphs (relationships between reference signs 31 and 32 of FIG. 2) regarding a subject with relatively fast heartbeat (the movement distance of the body tissue is relatively large) are illustrated by thick solid lines, and graphs (relationships between reference signs 31 and 33 of FIG. 2) regarding a subject with relatively slow heartbeat (the movement distance of the body tissue is relatively small) are illustrated by thin solid lines.

Figure 5:
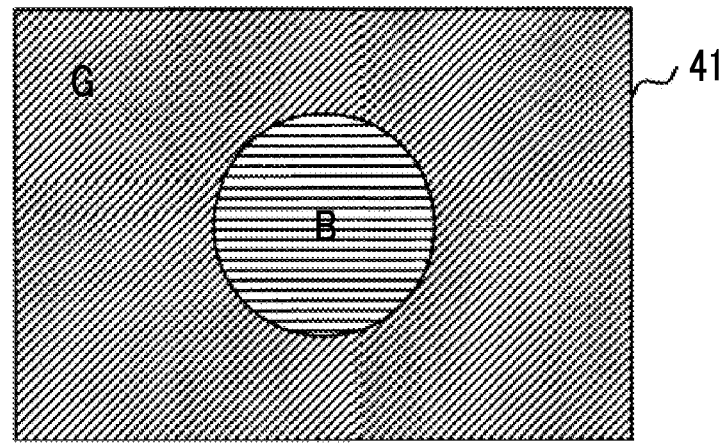
FIG. 5 schematically illustrates an elastic image regarding a subject with fast heartbeat.
Figure 6:
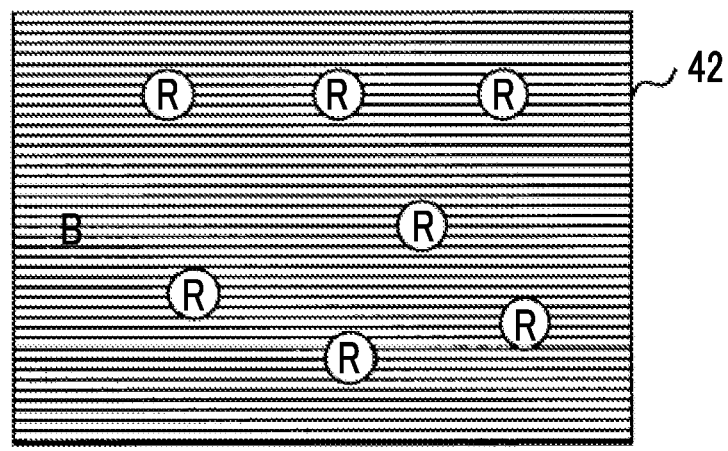
FIG. 6 schematically illustrates an elastic image regarding a subject with slow heartbeat.

FIG. 5 schematically illustrates an elastic image 41 regarding the subject with fast heartbeat, and FIG. 6 schematically illustrates an elastic image 42 regarding the subject with slow heartbeat. The elastic images represent the hardness (the magnitude of strain) of the body tissue. As an example of the methods of displaying the elastic images, the hardness of the body tissue can be represented by hues according to the degree of the hardness. In the elastic images, hard body tissue, that is, body tissue with small strain, is expressed in blue. Soft body tissue, that is, body tissue with great strain, is expressed in red. Body tissue with intermediate hardness is expressed in green. In FIGS. 5 and 6, a body tissue range displayed in blue is indicated by "B", a body tissue range displayed in red is indicated by "R", and a body tissue range displayed in green is indicated by "G". Here, assignment of the hues according to the hardness as an example of the methods for displaying the elastic images is not limited to the above, and can be arbitrarily set. Additionally, as another example of the methods for displaying the elastic images, the elastic images (the hardness of the body tissue) may be expressed by brightness, instead of the hues (color differences). That is, using specific hues, such as red, blue, and grayscales, for example, the hard body tissue, that is, the body tissue with small strain can be darkly expressed, and the soft body tissue, that is, the body tissue with great strain can be brightly expressed.

The elastic images are obtained by visibly expressing the strain representing the hardness of the body tissue calculated as described above. The strain is calculated by differentiating the movement distance (displacement) of the body tissue resulting from heartbeat (relationships between FIG. 3 and FIG. 4).

The tissue movement distance is calculated using a pair of ultrasonic frame data items at different acquisition times, which are obtained by ultrasonic measurement. The time interval between the pair of ultrasonic frame data items used for the calculation of the tissue movement distance is assumed to be constant. Regarding the subject with fast heartbeat, a substantially total range of tissue movement is acquired in the pair of ultrasonic frame data items at different acquisition times (the relationship between reference signs 31 and 32 of FIG. 2). That is, regarding the subject with fast heartbeat, a large movement distance is calculated using the pair of ultrasonic frame data items having a predetermined time interval, which are used for calculating the movement distance.

Next, a subject with extremely slow heartbeat will be considered. In a case where a pair of ultrasonic frame data items having the same time interval as the predetermined time interval at which the large movement distance can be calculated regarding the subject with fast heartbeat is used, a partial movement distance of tissue movement may not be acquired in the total range of the tissue movement regarding a subject with extremely slow heartbeat (the relationship between reference signs 31 and 33 of FIG. 2). In this case, a small movement distance is calculated.

Regarding the subject with fast heartbeat (the subject in which the large tissue movement distance is calculated between the pair of ultrasonic frame data items), referring to the graph of the thick solid lines of FIG. 3, a large difference is caused between the displacement of the soft peripheral tissue and the displacement of the hard diseased tissue (the inclination of the graph is completely different). Referring to the graph of the thick solid lines of FIG. 4, regarding the subject with fast heartbeat, the strain calculated by differentiating the displacement can be calculated to have a large value for the soft peripheral tissue and can be calculated to have a small value for the hard diseased tissue. Referring to FIG. 5, the blue B representing that the diseased tissue is hard (strain is small) is illustrated in the elastic image regarding the subject with fast heartbeat. A color (here, green G) showing that the peripheral tissue is softer than the diseased tissue is illustrated. The existence of the hard body tissue (diseased tissue) can be visually recognized.

In contrast, regarding the subject with extremely slow heartbeat (the subject in which the small tissue movement distance is calculated between the pair of ultrasonic frame data items), referring to the graph of the thin lines of FIG. 3, a difference is not recognized between the displacement of the peripheral tissue and the displacement of the diseased tissue and a noise signal may appear. In a case where this is differentiated, referring to the graph of the thin lines of FIG. 4, a value (noise) that does not originate from the difference between the hardness of diseased tissue, and the hardness of peripheral tissue will be calculated as the great strain.

Referring to FIG. 6, regarding the subject with slow heartbeat, a hue (here, red (R): color representing softness) affected by noise will appear in the elastic image. That is, the hardness of the body tissue cannot be accurately represented on the elastic image.

As illustrated in detail below, the ultrasonic diagnostic apparatus of this example keeps the movement distance of the body tissue between ultrasonic frame data items equal to or larger than a certain value and thereby prevents noise (FIG. 6) from appearing in the elastic image or makes noise less likely to appear in the elastic image, by calculating the average movement distance (an average value of the tissue movement distance between ultrasonic frame data items generated by the periodically repeated heartbeat) of the body tissue due to heartbeat and extending the time interval between the ultrasonic frame data items used to calculate the movement distance and used to generate an elastic image, in a case where the average movement distance of the body tissue caused by heartbeat is smaller than a predetermined threshold value (prescribed value).

In this example, the ultrasonic diagnostic apparatus using ultrasonic waves will be described. The present invention is not limited to the ultrasonic waves, and acoustic waves of audible frequencies may be used as long as a suitable frequency is selected in accordance with objects to be detected, measurement conditions, or the like.

Figure 7:
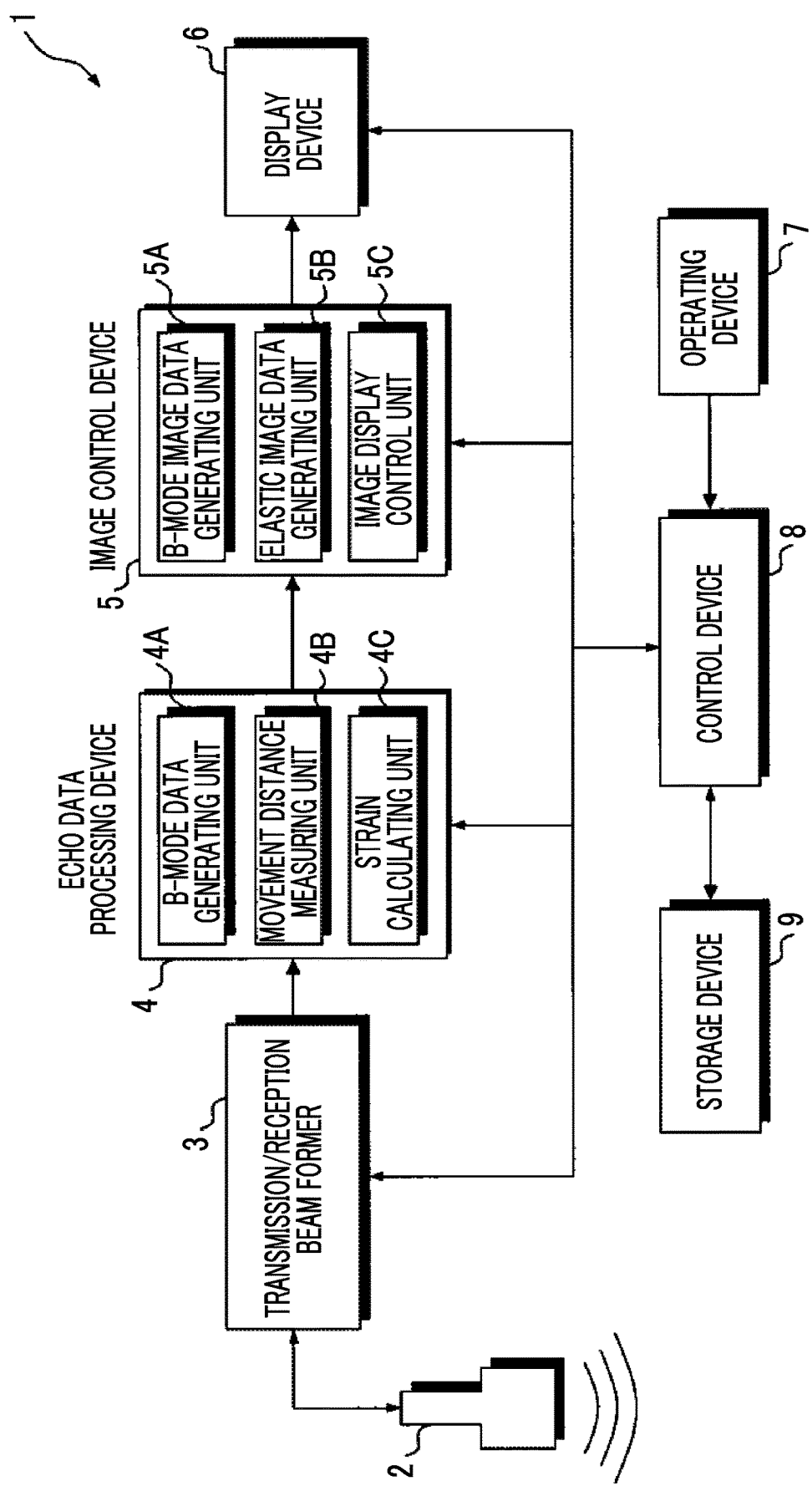
FIG. 7 is a block diagram illustrating an overall configuration of the ultrasonic diagnostic apparatus.

FIG. 7 illustrates a block diagram illustrating an overall configuration of an ultrasonic diagnostic apparatus 1. The ultrasonic diagnostic apparatus 1 includes an ultrasonic probe 2, a transmission/reception beam former 3, an echo data processing device 4, an image control device 5, a display device 6, an operating device 7, a control device 8, and a storage device 9.

The operation of ultrasonic diagnostic apparatus 1 is entirely controlled by the control device 8. A control program, a hue conversion look-up table, frame data, and the like for controlling the various devices (to be described in detail below) that constitute the ultrasonic diagnostic apparatus 1 are stored in the storage device 9 connected to the control device 8. An operator's instruction, a value to be set or adjusted, and the like are input from the operating device 7.

The ultrasonic probe 2 is pressed against the body surface of the subject (patient). The ultrasonic probe 2 transmits an ultrasonic beam toward the subject, receives an ultrasonic echo reflected from the body tissue within the subject, and outputs an ultrasonic echo signal representing the ultrasonic echo. The ultrasonic probe 2 having an arbitrary shape, such as a convex type, a sector type, or a linear type, can be used.

The transmission/reception beam former 3 drives the ultrasonic probe 2 under predetermined scanning conditions, and performs scanning with an ultrasonic beam. An arbitrary scanning method, such as sector scanning, offset sector scanning, or linear scanning, can be adopted. Additionally, the transmission/reception beam former 3 performs predetermined signal processing, such as phasing addition processing, on the ultrasonic echo signal from the ultrasonic probe 2, and generates ultrasonic frame data (tomographic echo data) corresponding to one scanning surface (one tomogram) of the body tissue. The generated ultrasonic frame data is sequentially stored in the storage device 9. The ultrasonic frame data is generated over time depending on a predetermined frame rate (the number of ultrasonic frame data items generated per unit time). The frame rate of the ultrasonic frame data can be changed by changing the transmission rate of the ultrasonic beam transmitted by the ultrasonic probe 2.

Next, the ultrasonic frame data is input to the echo data processing device 4. The echo data processing device 4 includes a B-mode data generating unit 4A, a movement distance measuring unit 4B, and a strain calculating unit 4C.

The B-mode data generating unit 4A performs logarithmic compression processing, envelope detection processing, or the like on the ultrasonic frame data to generate B-mode data.

The movement distance measuring unit 4B calculates the following movement distance, using the ultrasonic frame data. That is, the movement distance of each unit region (each pixel) is calculated on the basis of a pair of ultrasonic frame data items among a plurality of ultrasonic frame data items at different acquisition times, which are sequentially stored in the storage device 9, and the movement distance frame data is generated. Thereafter, a reference movement distance that is a representative value of the movement distance is calculated from the movement distance of each unit region. As the reference movement distance to be calculated, for example, an average value of movement distances for respective unit regions in a region of interest (ROI) set in a portion of an ultrasound image can be used. However, the movement distance of a specific unit region, such as the center of a frame, may be used as the reference movement distance, or a plurality of unit regions may be specified and an average value of the movement distance of the plurality of specified unit regions may be used. Moreover, a plurality of ROIs may be set, an average value of movement distances for respective unit regions in each ROI may be calculated regarding each of the set ROIs, the average of the average values calculated regarding the plurality of ROIs, respectively, may be further calculated. In addition, even in a case where the ROI is within a predetermined range, the ROI may be within a range specified using the operating device 7 by a user. Processing using the reference movement distance (representative value) will be described below.

The strain calculating unit 4C obtains the strain of each unit region on the basis of the movement distance frame data generated by the above-described movement distance measuring unit 4B, and generates strain frame data. The strain frame data is generated (calculated) by differentiating the movement distance frame data.

The B-mode data output from the B-mode data generating unit 4A of the echo data processing device 4 and the strain frame data output from the strain calculating unit 4C are input to the image control device 5. The image control device 5 includes a B-mode image data generating unit 5A, an elastic image data generating unit 5B, and an image display control unit 5C.

The B-mode image data generating unit 5A performs scanning conversion, using a scan converter on the B-mode data, and generates two-dimensional tomogram data (B-mode image data) suitable for the display in the display device 6. In the B-mode image data, signal intensity is represented by luminance. The B-mode image data has, for example, information representing the luminance of 256 gradations for each pixel.

The elastic image data generating unit 5B executes the processing of generating elastic image data in color representing the strain of each unit region in the strain frame data by a hue (a color difference) according to the magnitude of the strain, that is, making the strain into a hue. In the elastic image represented by the elastic image data, the magnitude of strain is represented by differences in hue. A correspondence relationship between the magnitude of strain and the hues is based on the hue conversion look-up table (not illustrated) stored in advance in the storage device 9.

The image display control unit 5C synthesizes the B-mode image data and the elastic image data, and generates synthesized image data. By the synthesized image data being transmitted to the display device 6, a synthesized ultrasound image in which a B-mode image and the elastic image are synthesized is displayed on a display screen of the display device 6. Indeed, the B-mode image and the elastic image may be displayed on the display screen without being synthesized.

Figure 8:
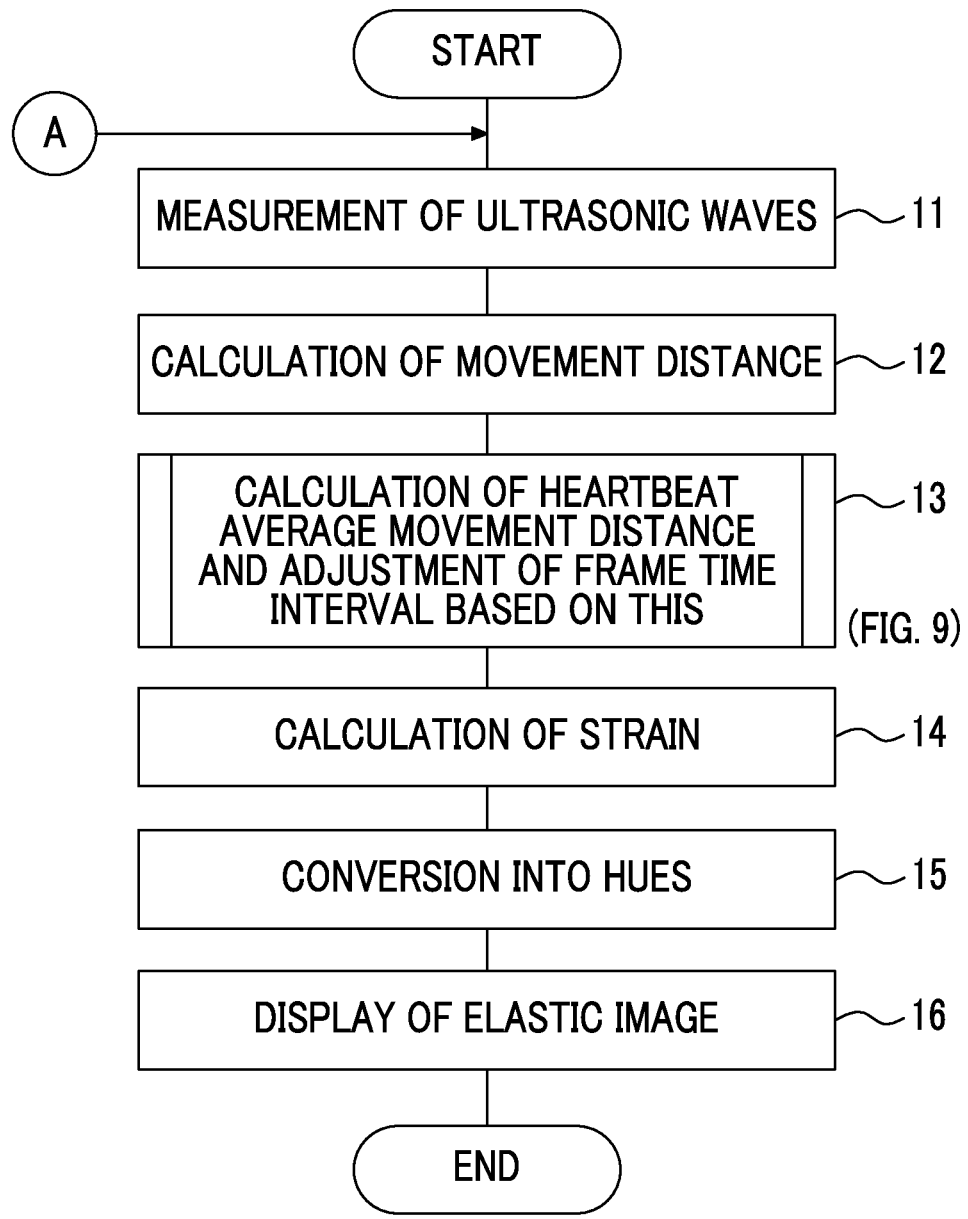
FIG. 8 is a flowchart illustrating a flow of processing for generating an elastic image.
Figure 9:
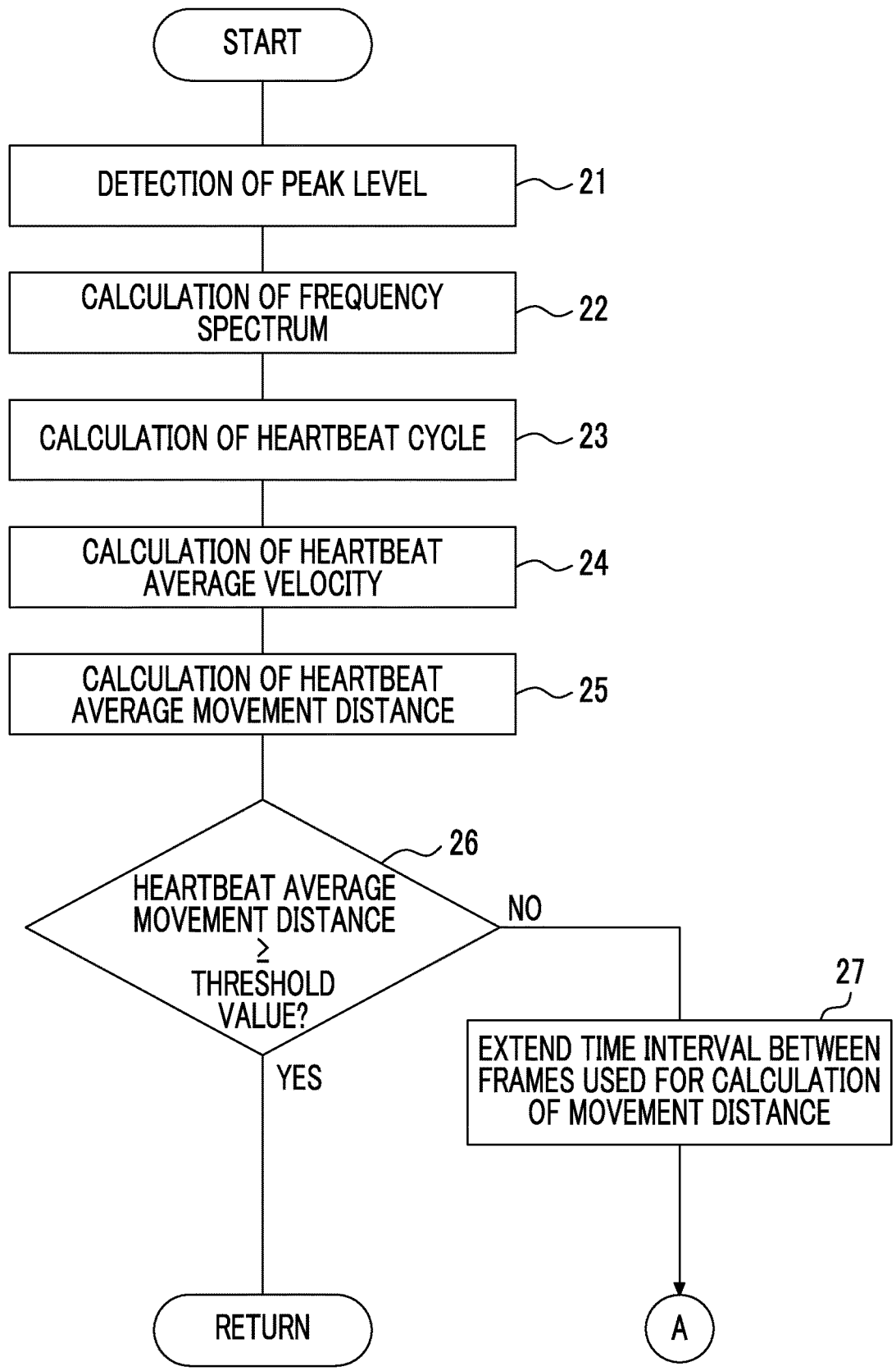
FIG. 9 is a flowchart illustrating a flow of the processing for generating the elastic image.

FIGS. 8 and 9 are flowcharts illustrating the processing of generating the elastic image data in the ultrasonic diagnostic apparatus 1.

Regarding a subject having a body tissue physically displaced due to heartbeat, ultrasonic frame data corresponding to one scanning surface (one tomogram) is continuously acquired (measurement of ultrasonic waves) (Step 11). The ultrasonic frame data is acquired at a predetermined frame rate, and is sequentially recorded in the storage device 9.

A pair of ultrasonic frame data items in the ultrasonic frame data sequentially recorded in the storage device 9 is used to calculate the movement distance of each unit region in the echo data processing device 4 and to generate movement distance frame data. Moreover, the above-described reference movement distance (representative value) is calculated (Step 12).

Figure 10:
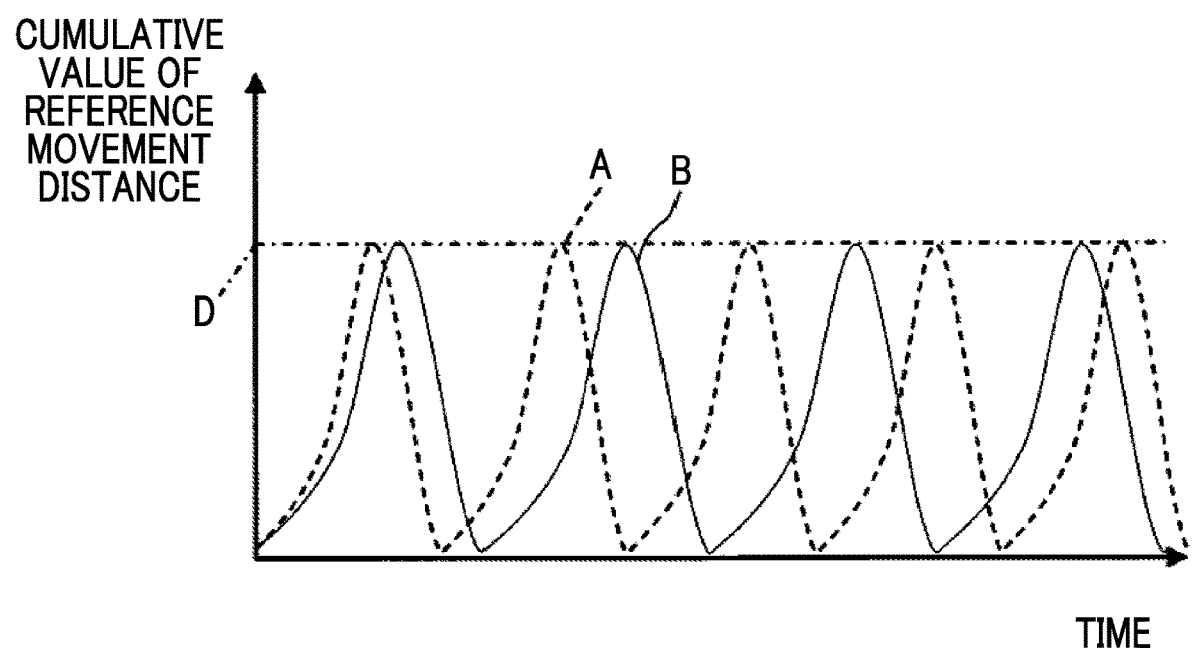
FIG. 10 is a graph illustrating the time variations of cumulative values of reference movement distances.

Data representing the reference movement distance for a certain time is stored in the storage device 9. FIG. 10 is a graph illustrating the time variations of cumulative values of reference movement distances for 5 seconds.

The time variation (dashed line A) of a cumulative value of the reference movement distance for 5 seconds in a subject A having a heartbeat of 60 times/min and the time variation (solid line B) of a cumulative value of the reference movement distance for 5 seconds in a subject B having a heartbeat of 48 times/min are illustrated in FIG. 10. The dashed line A of FIG. 10 records about five heartbeats (5 cycles). The solid line B records four heartbeats (4 cycles).

The data representing the cumulative values of the reference movement distances illustrated in FIG. 10 is used to calculate an average movement distance d of the body tissue between the pair of frame data items in the heartbeat equivalent to 1 cycle (hereinafter referred to as a heartbeat average movement distance d) and to perform the processing of adjusting the time interval of the frame data on the basis of the calculated heartbeat average movement distance d (Step 13). The calculation of the heartbeat average movement distance d and the adjustment of the time interval of the frame data are performed by the control device 8 along the following flow (FIG. 9).

First, the peak levels (peak movement distances) D (mm) of the cumulative values of the reference movement distances are detected (refer to FIG. 10) (Step 21). Here, in order to make this easily understood, the peak movement distances D of the subject A and the subject B are assumed to be the same.

Figure 11:
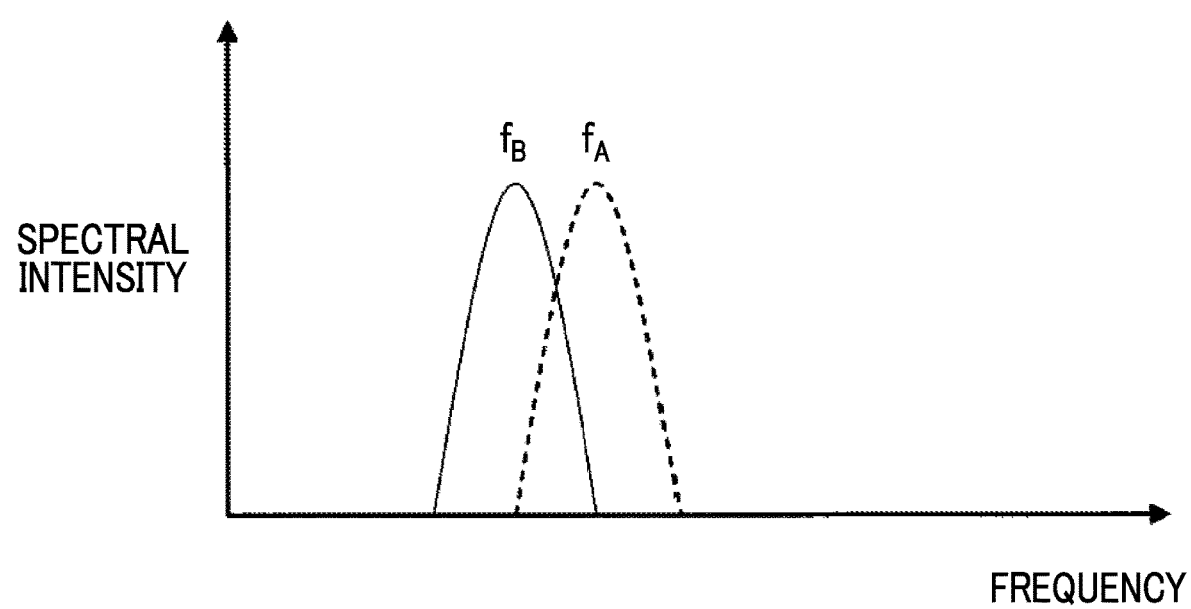
FIG. 11 illustrates frequency spectra corresponding to heartbeats.

Next, the data representing the cumulative values of the reference movement distances is subjected to fast Fourier transform (FFT), and frequency spectra are obtained (Step 22). FIG. 11 illustrates a frequency spectrum (dashed line) corresponding to the heartbeat of the subject A illustrated in FIG. 10, and a frequency spectrum (solid line) corresponding to the heartbeat of the subject B. For example, in a case where the frame rate of the ultrasonic frame data is assumed to be 30 [fps], the number of data items for 5 seconds is 30×5=150. Since it is desirable to have data items in the power of 2 in the FFT calculation, frequency spectra can be obtained using the most recent 128 data items.

Moreover, the peak levels of the frequency spectra are searched for, frequencies corresponding to the peak levels are determined as heartbeat frequencies, and heartbeat cycles (s) are obtained by calculating the inverses of the heartbeat frequencies [Hz] (Step 23). For example, in a case where the heartbeat frequency of the subject A is $f_A$=1.0 [Hz], the heartbeat cycle $T_A$ of the subject A is obtained as $T_A$=1.0 [s]. For example, in a case where the heartbeat frequency of the subject B is $f_B$=0.8 [Hz], the heartbeat cycle $T_B$ of the subject B is obtained as $T_B$=1.25 [s].

The body tissue repeats compression and relaxation due to heartbeat. It is possible that twice of the peak movement distance D is the total movement distance of the body tissue in the heartbeat equivalent to 1 cycle. Hence, the average velocity v [mm/s] of the heartbeat can be obtained by dividing the total movement distance 2D by the heartbeat cycle (2D/T) (Step 24). For example, regarding the above-described subject A of the heartbeat cycle $T_A$=1.0 [s], in a case where the peak movement distance is D=10 [mm], the heartbeat average velocity $v_A$ of $2D/T_A$=20/1=20 [mm/s] is calculated. Regarding the subject B of the heartbeat cycle $T_B$=1.25 [s], the heartbeat average velocity $v_B$ of $2D/T_B$=20/1.25=16 [mm/s] is calculated.

The frame rate of ultrasonic diagnostic apparatus 1 is defined as r [fps]. 1/r is equivalent to a time interval [s] between successive frames. The heartbeat average movement distance d is calculated by dividing the heartbeat average velocity by the frame rate r (multiplying the time interval 1/r between frames) (Step 25). In a case where the frame rate is set to 30 [fps], the heartbeat average movement distance $d_A$ of $v_A/r$=20/30=0.67 [mm] is calculated regarding the subject A. The heartbeat average movement distance $d_B$ of 16/30=0.53 [mm] is calculated regarding the subject B.

Special processing is not performed in a case where the heartbeat average movement distance d obtained as described above is equal to or greater than the predetermined threshold value (prescribed value) (YES in Step 26). On the other hand, in a case where the heartbeat average movement distance d is smaller than the threshold value, it is determined that the heartbeat is slow (or the frame rate is too high with respect to the rate of the heartbeat), and the processing of extending the time interval between the ultrasonic frame data items used for the calculation (Step 12) of the movement distance is performed (NO in Step 26, Step 27). The heartbeat average movement distance d can be increased by extending the time interval between the ultrasonic frame data items.

In a case where the heartbeat average movement distance d becomes smaller than the threshold value, noise appearing in an elastic image poses a problem. The maximum value of the heartbeat average movement distance d at which noise (refer to FIG. 6) appearing in an elastic image poses a problem is investigated, and the value is stored in the storage device 9 as the threshold value. Since the threshold value changes depending on the properties of an ultrasonic probe to be used, the threshold value may be stored in advance in association with an individual ultrasonic probe. However, the ultrasonic diagnostic apparatus 1 may enable its user to input the threshold value using the operating device 7 or to adjust the threshold value, using a slider bar between a predetermined maximum value and a predetermined minimum value.

Figure 12:
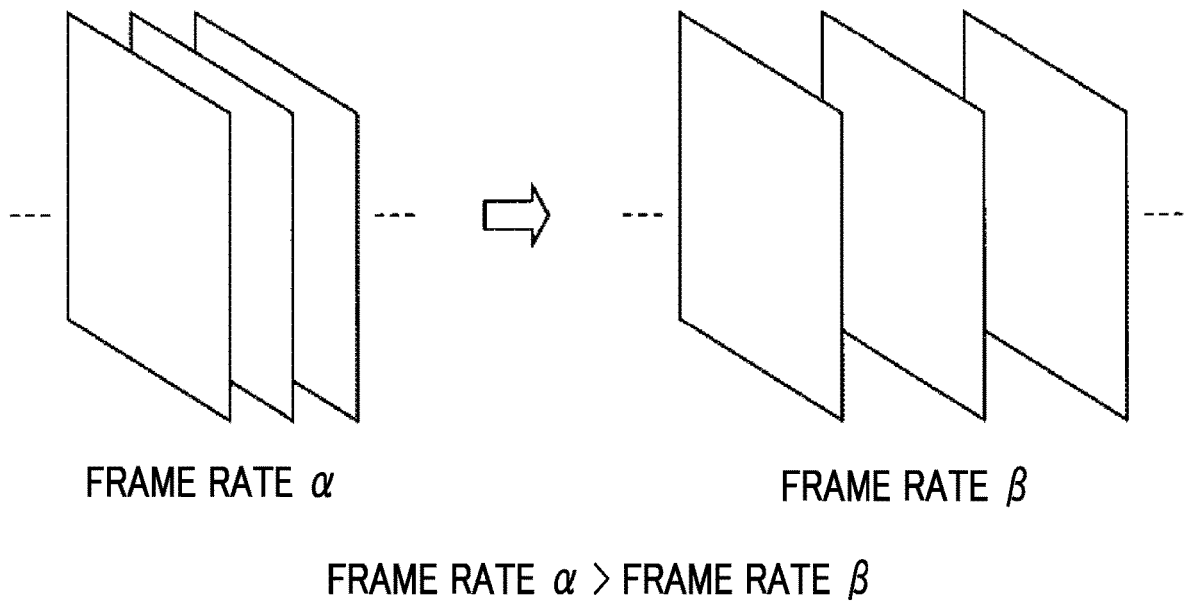
FIG. 12 illustrates an aspect in which the frame rate of the ultrasonic frame data is lowered.

As illustrated in FIG. 12, the time interval between the ultrasonic frame data used for the calculation of the movement distance can be extended by lowering the frame rate of the ultrasonic frame data. The frame rate of the ultrasonic frame data can be lowered by feedback-controlling the ultrasonic probe 2 and the transmission/reception beam former 3 by the control device 8 and changing the transmission rate of the ultrasonic beam.

The above time interval is adjusted such that the heartbeat average movement distance d has the threshold value. For example, in a case where the threshold value is 0.53 [mm], the calculated heartbeat average movement distance d is 0.47 [mm] (the heartbeat average velocity is 14 [mm/s] and the frame rate is 30 [fps]), the frame rate may be lowered such that the frame rate of the ultrasonic frame data has 14/0.53=26.42 [fps]. The heartbeat average movement distance d (14/26.42) can be made to substantially coincide with the threshold value.

Figure 13:
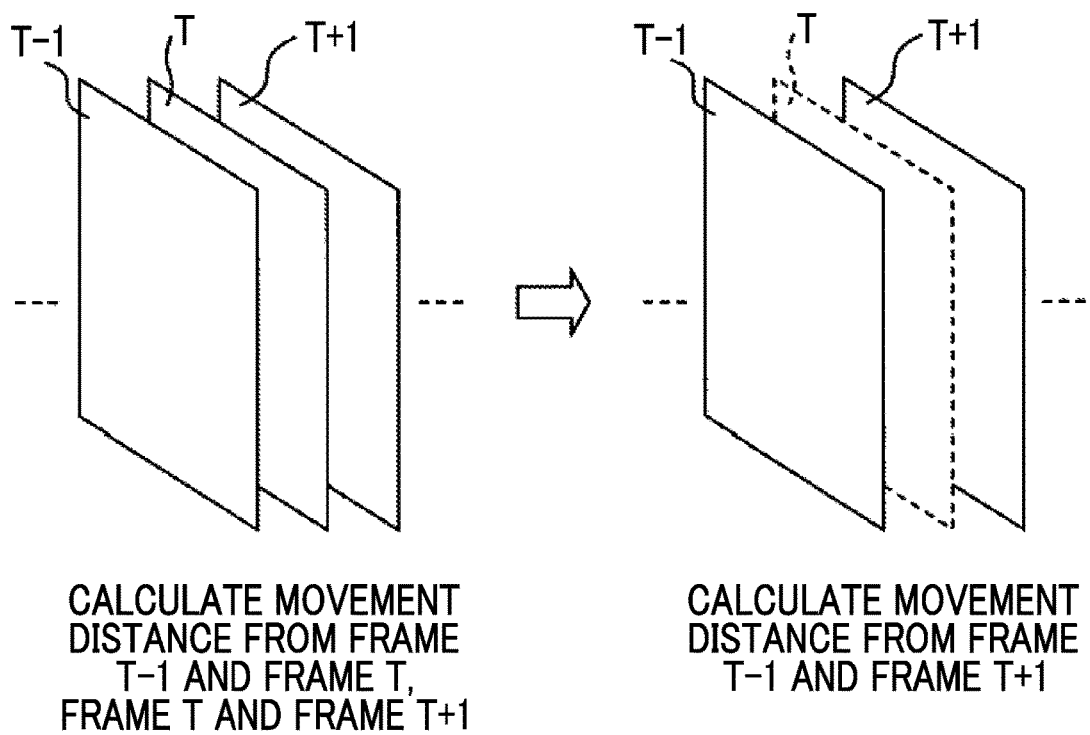
FIG. 13 illustrates an aspect in which the ultrasonic frame data is thinned out.

As illustrated in FIG. 13, the time interval between the ultrasonic frame data items used for the calculation of the movement distance may be extended not by changing the frame rate of the ultrasonic frame data but by, for example, alternately skipping (thinning out) the ultrasonic frame data items used for the calculation of the movement distance. This thinning-out processing is executed by feedback-controlling the echo data processing device 4 by the control device 8. Referring to FIG. 13, supposing the tissue movement distance is calculated using frame data T−1 and frame data T, and the frame data T and frame data T+1, which are continuously acquired before the adjustment of the time interval, the tissue movement distance is calculated from the frame data T−1 and the frame data T+1 after the adjustment of the time interval by the frame data T being thinned out. As a result, for example, in a case where the threshold value is 0.67 [mm] (20 [mm/s] in a case where the threshold value is expressed by heartbeat average velocity), and the calculated heartbeat average movement distance d is 0.33 [mm] (10 [mm/s] in a case where the threshold value is expressed by the heartbeat average velocity), the heartbeat average movement distance d can be made to coincide with the threshold value without lowering the frame rate of the ultrasonic frame data by keeping the frame rate of the ultrasonic frame data at 30 [fps] without being changed and alternately skipping the ultrasonic frame data used for the calculation of the movement distance as described above. Additionally, as described above, since the ultrasonic frame data is also used for the generation of the B-mode image, it is not necessary to lower the frame rate in the B-mode image.

In a case where the adjustment of the time interval of the ultrasonic frame data is performed as described above, the ultrasonic frame data acquired depending on the time interval after the adjustment is used, and the movement distance frame data is generated.

Referring back to FIG. 8, the strain of each unit region (each pixel) is calculated by differentiating the movement distance frame data in the echo data processing device 4, and the strain frame data is generated (Step 14). Next, in the image control device 5, strain frame data is converted into hues, using the hue conversion look-up table stored in advance in the storage device 9, and the elastic image data is generated by the hue conversion (Step 15). An elastic image in which the magnitude of strain is expressed by differences in hue is displayed on the display device 6 under the control of the image control device 5 (Step 16).

In this way, by adjusting the time interval between the ultrasonic frame data items that are used for the calculation of the movement distance and for the generation of the elastic image data such that the heartbeat average movement distance d reaches the predetermined threshold value, the movement of the body tissue exceeding the threshold value is detected. As a result, an elastic image affected slightly by noise (FIG. 5) or not affected by noise can be displayed.

Figure 14:
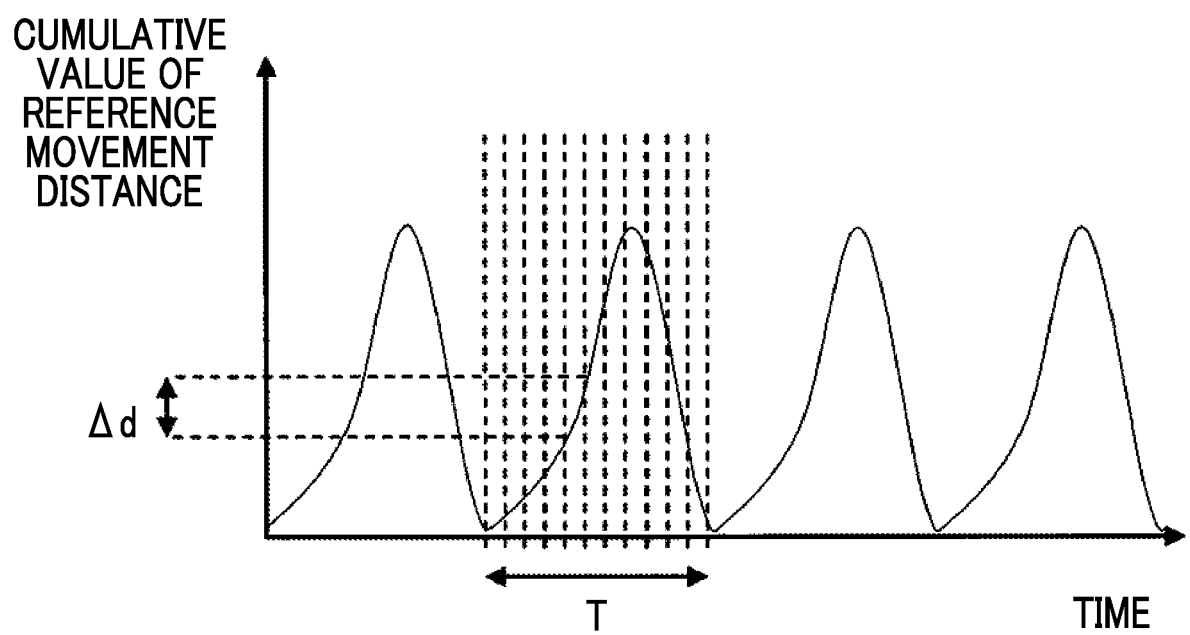
FIG. 14 illustrates movement distance $\Delta d$ calculated for a pair of ultrasonic frame data items in a plurality of ultrasonic frame data items acquired within a heartbeat cycle T.

In the above-described example, an example in which the average velocity v of the heartbeat is calculated and the heartbeat average movement distance d is calculated by dividing the average velocity by the frame rate r has been described. However, as illustrated in FIG. 14, the heartbeat average movement distance d can also be calculated by obtaining all movement distances Δd calculated for each pair of ultrasonic frame data items in a plurality of ultrasonic frame data items of the frame rate r acquired within the heartbeat cycle T after the heartbeat cycle T [s] is obtained and by taking the average of the movement distances (the average of integrated values). The heartbeat average movement distance d can be calculated by the following Formula.

$$d = \frac{\int_T |\Delta d|}{rT} \quad \text{[Formula 1]}$$

Instead of using all the movement distances Δd included in the heartbeat cycle T for the calculation of the heartbeat average movement distance d, the heartbeat average movement distance d may be calculated by excluding one or more movement distances Δd immediately after the start of the heartbeat and immediately before the end of the heartbeat among all the movement distances Δd included in the heartbeat cycle T, from calculation of the heartbeat average movement distance d. A situation in which the heartbeat average movement distance d may fluctuate vigorously due to extreme noise can be avoided. In that case, it is preferable to calculate the heartbeat average movement distance d by excluding movement distances Δd that belong to top N % and bottom N % (N is a real number of 10 or less) among all the movement distances Δd.

EXPLANATION OF REFERENCES

1: ultrasonic diagnostic apparatus (acoustic wave diagnostic apparatus)
2: ultrasonic probe (an acquisition device)
3: transmission/reception beam former (an acquisition device)
4: echo data processing device (a movement distance calculating device)
5: image control device (an elastic image generating device)
6: display device
7: operating device (a region-of-interest setting device)
8: control device (a heartbeat cycle calculating device, an average movement distance calculating device, an adjusting device)
9: storage device

What is claimed is:

1. An acoustic wave diagnostic apparatus comprising:
   a controller configured to:
      acquire acoustic wave frame data at a predetermined frame rate, using an acoustic wave echo signal representing an acoustic wave echo reflected from body tissue of a subject;
      calculate a movement distance of the body tissue, using a pair of acoustic wave frame data items;
      generate an elastic image representing strain calculated from the movement distance of the body tissue that is calculated;
      calculate a heartbeat cycle by inverting a frequency peak from a frequency spectra corresponding to the movement distance of the body tissue;
      calculate an average movement distance of the body tissue between the acoustic wave frame data items in the heartbeat cycle of the subject, using a movement distance of the body tissue determined from each of a plurality of pairs of acoustic wave frame data items and the calculated heartbeat cycle; and
      extend a time interval between the acoustic wave frame data items to calculate a subsequent movement distance of the body tissue from elastic images based on thresholding,
      wherein the time interval extension is executed by thinning out the acoustic wave frame data while maintaining the predetermined frame rate in a case where the average movement distance is smaller than a predetermined threshold, and
      wherein the subsequent movement distance is calculated based on the time interval that is extended.

2. A method of controlling an acoustic wave diagnostic apparatus comprising:
   acquiring acoustic wave frame data at a predetermined frame rate, using an acoustic wave echo signal representing an acoustic wave echo reflected from body tissue of a subject;
   calculating a movement distance of the body tissue, using a pair of acoustic wave frame data items;
   generating an elastic image representing strain calculated from the movement distance of the body tissue that is calculated;
   calculating a heartbeat cycle by inverting a frequency peak from a frequency spectra corresponding to the movement distance of the body tissue;
   calculating an average movement distance of the body tissue between the acoustic wave frame data items in the heartbeat cycle of the subject, using a movement distance of the body tissue determined from each of a plurality of pairs of acoustic wave frame data items and the calculated heartbeat cycle; and
   extending a time interval between the acoustic wave frame data items to calculate a subsequent movement distance of the body tissue from elastic images based on thresholding,
   wherein the time interval extension is executed by thinning out the acoustic wave frame data while maintaining the predetermined frame rate in a case where the average movement distance is smaller than a predetermined threshold, and
   wherein the subsequent movement distance is calculated based on the time interval that is extended.

* * * * *